(12) United States Patent
Tomalia et al.

(10) Patent No.: US 6,475,994 B2
(45) Date of Patent: Nov. 5, 2002

(54) METHOD AND ARTICLES FOR TRANSFECTION OF GENETIC MATERIAL

(75) Inventors: Donald A. Tomalia, 463 W. Chippewa River Rd., Midland, MI (US) 48640; Lajos Balogh, Ann Arbor, MI (US)

(73) Assignee: Donald A. Tomalia, Midland, MI (US)

( * ) Notice: Subject to any disclaimer, the term of this patent is extended or adjusted under 35 U.S.C. 154(b) by 0 days.

(21) Appl. No.: 09/219,907

(22) Filed: Dec. 23, 1998

(65) Prior Publication Data

US 2002/0013283 A1 Jan. 31, 2002

Related U.S. Application Data

(60) Provisional application No. 60/070,666, filed on Jan. 7, 1998.

(51) Int. Cl.$^7$ .............................................. A61K 31/70
(52) U.S. Cl. ..................... 514/44; 435/91.4; 435/320.1; 435/455; 424/486; 424/497
(58) Field of Search ............................ 435/320.1, 69.1, 435/325, 455, 458; 514/44; 424/486, 497

(56) References Cited

U.S. PATENT DOCUMENTS

| | | | | |
|---|---|---|---|---|
| 4,945,050 A | * | 7/1990 | Sanford ....................... | 435/455 |
| 5,527,524 A | * | 6/1996 | Tomalia et al. ............ | 424/1.33 |
| 5,714,166 A | * | 2/1998 | Tomalia et al. ............. | 424/486 |
| 5,919,442 A | * | 7/1999 | Yin et al. ................. | 424/78.18 |
| 5,962,427 A | * | 10/1999 | Goldstein et al. ............. | 514/44 |
| 5,972,720 A | * | 10/1999 | Nichtl et al. ................ | 436/525 |

FOREIGN PATENT DOCUMENTS

| | | | |
|---|---|---|---|
| EP | 0684044 | * | 11/1995 |
| WO | 94/23738 | * | 10/1994 |

OTHER PUBLICATIONS

Nanoparticles of Ag, Au, Pd, and Cu Produced By Alcohol Reduction Of The Salts, S. Ayyappan, G.N. Subbanna, C.N.R. Rao$^{a)}$, J.Master. Res., vol. 12, No. 2, Feb. 1997, pp. 398–401.
Rough Guide To The Nanoworld, Paul Calvert.
Nature—vol. 383, Sep. 26, 1996, pp. 300–301.
Novel Approach For The Preparation Of Metal Colloid Monolayers On Modified Surfaces, Shai Rubin, George Bar,$^{a)}$.
Thomas N. Taylor, Russell W. Cutts, and Thomas A. Zawodzinski, Jr.$^{b)}$, J. Vac. Sci. Technol. A 14(3), May/Jun. 1996, pp. 1870–1877.
Gene Therapeutics Methods and Applications of Direct Gene Transfer, Jon A. Wolff, Editor, ©1994 Birkhäuser Boston pp. 194–209.

* cited by examiner

*Primary Examiner*—Dave T. Nguyen
(74) *Attorney, Agent, or Firm*—Karen L. Kimble

(57) ABSTRACT

A gene transfection particle includes a polymer, a support particle conjugated with the dendritic polymer, and genetic material conjugated with the dendritic polymer. The gene transfection particles are highly efficient and are capable of delivering higher quantities of genetic materials to cells, with reduced cell damage. A gene transfection method involves bombarding cells with conjugates of polymers and genetic material, with or without a support particle.

18 Claims, No Drawings

METHOD AND ARTICLES FOR TRANSFECTION OF GENETIC MATERIAL

CLAIM OF PRIORITY

Applicant(s) hereby claim the priority benefits under the provisions of 35 U.S.C. §119, basing said claim of priority on U.S. Provisional Patent Application No. 60/070,666, filed Jan. 7, 1998.

FIELD OF THE INVENTION

This invention relates to compositions of matter and methods which are useful in delivering genetic materials to the interior of plant and animal cells, and more particularly to gene transfection particles and particle bombardment methods for gene transfection.

BACKGROUND OF THE INVENTION

Particle bombardment, also know as the gene gun method, provides a potentially effective method for introducing genetic materials into plant and animal cells in the treatment and control of a variety of genetic, neoplastic and infectious diseases, and for creating transgenic species. Particle bombardment methods of introducing genetic materials into plant and animal cells involves accelerating microscopic particles coated with a genetic material through the wall of the cell to deliver the genetic material to the interior of the cell. The motive force used to accelerate the particles can be generated by high-voltage electric discharge, helium pressure discharge or other means. The microscopic projectile transfection particles generally comprise a gold particle having a diameter of from about 1 to 15 micrometers, and genetic materials attached thereto. Gold particles are preferred because they are chemically inert, have no cytotoxic effects in the cells, and have a high density which permits greater momentum and penetration into cells. Binding agents such as spermidine (N-3-aminopropyl-1-4-butanediamine) have been used to attach genetic materials to gold particles.

A disadvantage with known particle bombardment methods is that they may not provide a sufficient quantity of genetic material to achieve a desired therapeutic effect without causing unacceptably high levels of cell damage. Ning-Sun Yong et al., in Gene Therapeutics: Methods and Applications of Direct Gene Transfer, have reported that for confluent monolayer cell cultures with cells 15–20 micrometers in size, a particle bombardment density of 0.1 particles per square centimeter of 0.9 micrometer particles, which delivers about two particles per cell, results in more than 90% of monolayer cells and 75% of suspension cells being viable and healthy after particle bombardment, but that for most tissue samples, higher particle bombardment densities cause excessive cell and tissue damage. Because of the relatively low binding capacity of the linear polyamines used to attach genetic materials to gold particles, and the relatively low levels of particle bombardment which can be tolerated without excessive cell damage, known transfection particles may not be capable of introducing sufficient quantities of genetic materials to cells to achieve a desired therapeutic or other effect while avoiding excessive cell damage.

Accordingly, there is a need for transfection particles which are capable of delivering higher amounts of genetic materials into cells using particle bombardment methods while minimizing cell damage.

SUMMARY OF THE INVENTION

The invention provides highly efficient transfection particles and bombardment methods which are capable of delivering higher amounts of genetic materials to cells while minimizing cell damage. The gene transfection particles of this invention comprise a composite material including a polymer, a support particle conjugated with the polymer, and genetic material conjugated with the polymer.

The bombardment method of this invention involves the steps of forming a gene transfection particle including a polymer, and genetic material conjugate, with or without a support particle, and accelerating the gene transfection particle toward a cell with sufficient motive force to cause the gene transfection particle to penetrate and enter the cell.

An advantage of the invention is that it provides a method whereby the density of the gene transfection particles can be adjusted as required depending on the robustness of the cell membrane which must be penetrated.

DESCRIPTION OF THE PREFERRED EMBODIMENTS

The gene transfection particles of the preferred embodiment of the invention preferably include genetic material which is conjugated to polymer, and a metal, in the form of one or more atoms, one or more ion complexes, clusters, or particles, or other support which is also conjugated to the polymer. The metal component provides the gene transfection particles with the density needed to achieve the momentum which is necessary to penetrate the cell wall and/or membrane when the particles are accelerated toward the cell so that the carried genetic material can be delivered to the interior of the cell. The metal used in preparing the gene transfection particles must be chemically inert in the cell environment, have essentially no, or at least very low, cytotoxic effects in the cells, and be capable of being conjugated to a dendritic polymer. The metal preferably has a relatively high density to allow greater momentum and, hence, adequate penetration of the cell wall and/or membrane. Gold is presently preferred because of its established acceptance for use in gene therapy. However, other metals may be employed in certain applications. Examples of metals which may be suitable for use in particle bombardment gene therapy methods include gold, tungsten, silver, copper, magnesium, calcium and combinations thereof.

The metal component may be conjugated to the dendritic polymer in the form of an individual atom, ion, or complex, or in the form of clusters of atoms or microscopic size particles. In addition to metal particles, other suitable supports includes silica particles, alumina particles, and other solid supports having Lewis acid surface functionality. Also, it has been determined that dendritic polymers conjugated to genetic materials, without any metals or other support materials conjugated thereto may also be usefully employed as gene transfection particles in particle bombardment methods.

The gene transfection particles prepared by contacting a dendritic polymer with a metal atom or a metal atom-containing entity, and a genetic material may have a diameter or maximum dimension of from about 1 nm to about 15 nm. Particles comprised of dendritic clusters or aggregates can have a maximum dimension of from about 2 nm up to at least several micrometers. However, the gene transfection particles of this invention preferably have a particle size of from about 1 nm to about 1000 nm, and more preferably from about 1 nm to about 100 nm.

The genetic materials which may be used in preparing the gene transfection particles of this invention include biological response modifiers, such as interleukins, interferons, and viruses, viral fragments and other genetic materials. The term "genetic material" as used herein refers to nucleotide based materials, including without limitation, viruses and viral fragments, deoxyribonucleic acid (DNA), plasmids, ribonucleic acid (RNA), messenger RNA (mRNA), transfer RNA (tRNA), ribosomal RNA (rRNA), catalytic RNA (cRNA), smaller nuclear RNA (snRNA), exons, introns, codons, and anti-sense oligonucleotides. Genetic material, especially viruses and viral fragments, may incidentally include some protein.

The polymers are preferably dendritic, but linear and other non-dendritic polymers may be suitable. The dendritic polymers used in preparing the gene transfection particles of the preferred embodiment include generally any dendritic polymers which include functional groups, on the interior and/or exterior, which are capable of binding or conjugating the metal with the dendritic polymer. The dendritic polymers used to coat the metal particles have surface functional groups which have an affinity for (i.e., will stick to) the surface of the support particles, with the preferred dendritic polymers being those having amine functional groups e.g., such as PAMAM, POPAM and PEI dendritic polymers. The support particles and the dendritic polymers are contacted under conditions sufficient to cause the dendritic polymer molecules to adhere to the surface of the support particles. Thereafter, the dendritic polymer-support particle conjugate is contacted with genetic material to form a highly efficient gene transfection particle which is capable of delivering larger quantities of genetic materials to a cell, as compared with known gene transfection particles. This result can be achieved even with particles which are substantially smaller than known gene transfection particles, resulting in improved therapeutic effect and reduced cell damage.

Dendritic polymers which may be used include generally any of the known dendritic architectures including dendrimers, regular dendrons, controlled hyperbranched polymers, dendrigrafts, and random hyperbranched polymers. Dendritic polymers are polymers with densely branched structures having a large number of reactive groups. A dendritic polymer includes several layers or generations of repeating units which all contain one or more branch points. Dendritic polymers, including dendrimers and hyperbranched polymers, are prepared by condensation reactions of monomeric units having at least two reactive groups. The dendrimers which can be used include those comprised of a plurality of dendrons that emanate from a common core which can be a single atom or a group of atoms. Each dendron generally consists of terminal surface groups, interior branch junctures having branching functionalities greater than or equal to two, and divalent connectors that covalently connect neighboring branching junctures.

Dendrons and dendrimers can be prepared by convergent or divergent synthesis.

Divergent synthesis of dendrons and dendrimers involves a molecular growth process which occurs through a consecutive series of geometrically progressive step-wise additions of branches upon branches in a radially outward molecular direction to produce an ordered arrangement of layered branched cells. Each dendritic macromolecule includes a core cell, one or more layers of internal cells, and an outer layer of surface cells, wherein each of the cells includes a single branch juncture. The cells can be the same or different in chemical structure and branching functionality. The surface branch cells may contain either chemically reactive or passive functional groups. Chemically reactive surface groups can be used for further extension of dendritic growth or for modification of dendritic molecular surfaces. The chemically passive groups may be used to physically modified dendritic surfaces, such as to adjust the ratio of hydrophobic to hydrophilic terminals, and/or to improve the solubility of the dendritic polymer for a particular solvent Convergent synthesis of dendrimers and dendrons involves a growth process which begins from what will become the surface of the dendron or dendrimer and progresses radially in a molecular direction toward a focal point or core. The dendritic polymers may be ideal or non-ideal, i.e., imperfect or defective. Imperfections are normally a consequence of either incomplete chemical reactions, or unavoidable competing side reactions. In practice, real dendritic polymers are generally nonideal, i.e., contain certain amounts of structural imperfections.

The hyperbranched polymers which may be used represent a class of dendritic polymers which contain high levels of nonideal irregular branching as compared with the more nearly perfect regular structure of dendrons and dendrimers. Specifically, hyperbranched polymers contain a relatively high number of irregular branching areas in which not every repeat unit contains a branch juncture. The preparation and characterization of dendrimers, dendrons, random hyperbranched polymers, controlled hyperbranched polymers, and dendrigrafts is well known. Examples of dendimers and dendrons, and methods of synthesizing the same are set forth in U.S. Pat. Nos. 4,507,466; 4,558,120; 4,568,737; 4,587,329; 4,631,337; 4,694,064; 4,713,975; 4,737,550; 4,871,779 and 4,857,599. Examples of hyperbranched polymers and methods of preparing the same are set forth, for example in U.S. Pat. No. 5,418,301.

The dendritic polymers or macromolecules useful in the practice of this invention are characterized by a relatively high degree of branching, which is defined as the number average fraction of branching groups per molecule, i.e., the ratio of terminal groups plus branch groups to the total number of terminal groups, branched groups and linear groups. For ideal dendrons and dendrimers, the degree of branching is 1. For linear polymers, the degree of branching is 0. Hyperbranched polymers have a degree of branching which is intermediate that of linear polymers and ideal dendrimers, a degree of branching of at least about 0.5 or higher is preferred. The degree of branching is expressed as follows:

$$f_{br} = \frac{N_t + N_b}{N_t + N_b + N_l}$$

where $N_x$ is the number of type x units in the structure. Both terminal (type t) and branched (type b) units contribute to the fully branched structure whilst linear (type l) units reduce the branching factor; hence $$0 \leq f_{br} \leq 1$$

where $f_{br}=0$ represents the case of a linear polymer and $f_{br}=1$ represents the case of a fully branched macromolecule.

Dendritic polymers suitable for use with the invention also include macromolecules commonly referred to as cascade molecules, arborols, arborescent grafted molecules, and the like. Suitable dendritic polymers also include bridged dendritic polymers, i.e., dendritic macromolecules linked together either through surface functional groups or through a linking molecule connecting surface functional groups together, and dendritic polymer aggregates held together by physical forces. Also included are sphericalshaped dendritic polymers and rod-shaped dendritic polymers grown from a polymeric core.

The dendritic polymers used in the practice of this invention can be generationally monodisperse or generationally polydisperse. Dendritic polymers in a monodisperse solution are substantially all of the same generation, and hence of uniform size and shape. The dendritic polymers in the polydisperse solution comprise a distribution of different generation polymers. The dendritic polymer molecules which may be used in the practice of this invention include mixtures of different interior and exterior compositions or functionalities.

Dendritic polymers which are useful in the practice of this invention include those that have symmetrical branch cells (arms of equal length, e.g., PAMAM dendrimers) and those having unsymmetrical branch cells (arms of unequal length, e.g. lysine-branched dendrimers) branched dendrimers, cascade molecules, arborols, and the like.

The term "dendritic polymer" also includes so-called "hyper comb-branched" polymers. These comprise non-crosslinked poly-branched polymers prepared by (1) forming a first set of linear polymer branches by initiating the polymerization of a first set of monomers which are either protected against or non-reactive to branching and grafting, during polymerization, each of the branches having a reactive end unit upon completion of polymerization, the reactive end units being incapable of reacting with each other; (2) grafting the branches to a core molecule or core polymer having a plurality of reactive sites capable of reacting, with the reactive end groups on the branches; (3) either deprotecting or activating a plurality of monomeric units on each of the branches to create reactive sites; (4) separately forming a second set of linear polymer branches by repeating step (1) with a second set of monomers; (5) attaching the second set of branches to the first set of branches by reacting the reactive end groups of the second set of branches with the reactive sites on the first set of branches, and then repeating steps (3), (4) and (5) above to add one or more subsequent sets of branches. Such hyper comb-branched polymers are disclosed in European Patent Publication 0473088A2. A representative formula for such hyper comb-branched polymer is:

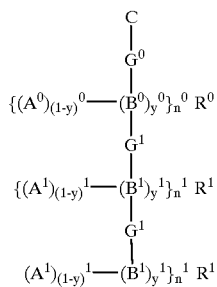

wherein C is a core molecule; each R is the residual moiety of an initiator selected from a group consisting of free radical initiators, cationic initiators, anionic initiators, coordination polymerization initiators and group transfer initiators; A and B are polymerizable monomers or comonomers capable of withstanding the conditions required for branching therefrom or grafting thereto, at least during the polymerization of the $\{(A)-(B)\}$ linear polymer chain and during its grafting to a prior $\{(A)-(B)\}$ branch of the $\{(A)-(B)\}$ core branch; each G is a grafting component, and the designation

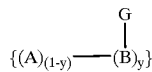

$\{(A)_{(1-y)}-(B)_y\}$ indicates that G can attach to either an (A) unit or a (B) unit; n is the degree of polymerization of the indicated generation comb-branches; y is the fraction of B units in the indicated generation branch, and has a value of 0.01 to 1; the superscripts 0, 1 and i designate the comb-branch generation level, with i beginning at "2" and continuing for the number of reiterative branch set generations in the polymer; and at least $n^0$ and n' are $\geq 2$.

For purposes of clarifying terminology, it should be noted that dense star dendrimers are built by reiterative terminal branching, while hyper comb-branched dendrimers are built by reiterative comb-branching. In dense star dendrimers, subsequent generation branches are attached to the terminal moieties of a previous generation, thus limiting the degree of branching to the functionality of the previous generation terminal moiety, which would typically be two or three. In contrast, by branching oligomers upon prior generation oligomer branches in accordance with hyper comb-branched dendrimer, one can dramatically increase the degree of branching from generation to generation, and indeed can vary the degree of branching from generation to generation.

Dendritic polymers which are particularly well suited for use in preparing the gene transfection particles of this invention include various dendritic polymers containing exterior and/or interior primary or secondary amine groups, amide groups, or combination thereof. Examples include polyamidoamine (PAMAM) dendritic polymers, polypropylamine (POPAM) dendritic polymers, and polyethyleneimine (PEI) dendritic polymers. Dendritic polymers having amide and/or amine groups have a very high affinity and binding capacity for both metals and genetic materials.

In accordance with a preferred aspect of the invention, a support particle, preferably of metal is first conjugated with a dendritic polymer to form a metal/dendrimer composite which is subsequently contacted with a genetic material to form gene transfection particles. Conjugation, as used herein, refers to any of various interactions between the dendritic polymer and the support, in which the support is bonded to the dendritic polymer or otherwise localized with respect to the dendritic polymer so that the density of the support can be utilized to impart sufficient momentum to the gene transfection particle during particle bombardment to achieve cell penetration and introduction of the genetic material to the cell interior. Thus, conjugation, as used herein, encompasses chemical bonding, such as complexation, hydrogen bonding, dipole-dipole interactions, London dispersion forces, Van der Waals interactions, as well as physical entrapment or diffusion controlled retention of the support within the interior of a dendritic polymer.

The metal which is conjugated with the dendritic polymer can be in the form of individual metal atoms or metal atom-containing moieties which are bonded to functionally reactive sites within the interior or on the exterior of a dendritic polymer molecule, or physically entrapped or retained within the interior of the dendritic polymer molecule. The metal which is conjugated with the dendritic polymer may also be in the form of a cluster of metal atoms or a metal particle to which the dendritic polymer(s) is bonded.

Metal-dendritic polymer conjugates or composites in which the metal is in the form of a metal atom or metal atom-containing moiety bound to, trapped within, or retained within a dendritic polymer molecule can be prepared by localizing a metal atom-containing entity (such as a metal atom, a metal ion, or metal-containing complex or molecule) with respect to a dendritic polymer. Localization, as used herein, involves contacting the dendritic polymer with a metal atom-containing entity under suitable conditions for a suitable period to allow the metal atom-containing entity to become chemically conjugated with interior or exterior reactive sites, or both, and/or disposed within the interior of the dendritic polymer molecule. Physical restraint may range from relatively transient containment of the reactant or reactants within the interior of the dendritic polymer to relatively permanent entrapment of the reactant or reactants in the interior or exterior of the dendritic polymer. Bonding of the reactant or reactants with the interior or exterior of the dendritic polymer includes ionic bonding, donor acceptor interactions (coordination bonding), hydrogen bonding, Van der Waal interactions, and London dispersion interactions. Metal atom-containing entities can become physically entrapped within the interior of a dendritic polymer by contacting a metal atom-containing entity with a dendritic polymer having an interior which is accessible to the metal atom-containing entity, under conditions and for a period sufficient to allow the metal atom-containing entities to become disposed within the interior of the dendritic polymer molecule, and thereafter reacting the metal atom-containing entity to form a compound or ion which is physically trapped within the interior of the dendritic polymer molecule, and/or modifying the surface of the dendritic polymer molecule so that the dendrimer is no longer permeable to the metal atom-containing entity. For example, metal ions can generally enter the interior defined by generation 4 through 6 PAMAM dendrimers, and subsequently react with a complexing agent which is also capable of permeating the dendrimer surface to form a complex which is incapable of leaving the interior of the dendrimer on account of its physical size and/or shape. Methods for trapping metal atom-containing entities within the interior of a dendritic polymer by modifying the surface groups are disclosed, for example, in European Patent Application 95 201373.8 (Publication No. 0,684,044 A2).

The metal-dendritic polymer conjugates in which the metal is distributed on and/or within the dendritic polymer in the form of individual atoms or moieties containing a single metal atom can be contacted with genetic material to form gene transfection particles. All genetic materials contain an acid functionality which will readily and tenaciously bond with various surface functionally reactive sites on dendritic polymers, especially with amine and amide functional groups. Because of the very high surface density of functional groups on dendritic polymers (for example, a fifth generation PAMAM dendrimer has 128 amine bonding sites) relatively high amounts of genetic material can be conjugated to a dendritic polymer to form gene transfection particles having a much higher level of genetic material to particle mass and size than the known gene transfection particles. As a result, effective amounts of genetic material can be delivered to the interior of a cell using fewer particles, and using smaller particles. Each of these factors may contribute to lower levels of cell damage during particle bombardment, and, therefore, higher levels of cell and tissue viability after particle bombardment.

The metal-dendritic polymer conjugates described above may be combined or conjugated, to each other or to dendritic polymers which do not include any metal, to form dendritic polymer clusters or aggregates having a larger diameter or maximum dimension than a single dendritic polymer molecule. Conjugation of dendritic polymers into clusters or aggregates can be achieved by coordination bonding of at least two different dendritic polymer molecules to a single metal atom, or by use of divalent, trivalent or other polyvalent crosslinking agents, which may be linear or branched polymers or other macromolecules, including dendritic polymers having surface functional groups which will bond directly with the surface functional groups of other dendritic polymers. When two or more different types of dendritic polymers having different types of surface functional groups are used to form metal-dendritic polymer clusters by direct reaction of the different types of surface functional groups with each other, the different types of dendrimers may be first reacted with each other to form clusters or aggregates, and subsequently contacted with a metal atom-containing entity, or one or more different types of dendritic polymers may be contacted with a metal atom-containing entity to form one, or more, metal-dendritic polymer conjugate(s) which is, or are, subsequently reacted with the other dendritic polymer(s) and/or metal-dendritic polymer conjugate (s) to form dendritic polymer cluster or aggregates containing metal.

The genetic material may be contacted with the dendritic polymer, or polymers, before, during, or after the dendritic polymer, or polymers, have been contacted with the metal atom-containing entity, or entities, or a combination thereof.

The metal and genetic material loading can be controlled as desired, such as by carefully controlling the quantities of materials which are contacted with each other, by the selection of the dendritic polymer or polymers with respect to type, size, generation and surface functionality, by controlling the conditions under which the components are contacted, etc.

By suitable selection of the dendritic polymer or polymers, crosslinkers, if any, the type and amount of the metal atom-containing entity or entities, the loading level of metal and genetic material, the manner in which and the conditions under which the components are combined, any of various particle sizes, particle densities and therapeutic activities can be achieved to meet specific requirements relating to the type of cell being treated and the type of disease which is being treated.

In accordance with another aspect of the invention, the gene transfection particles can be prepared by coating dendritic polymer molecules onto the surface of a metal particle. Suitable gold particles, provided in the form of gold sols, are commercially available from a variety of different suppliers.

Preferred metal particles in accordance with this invention have a diameter or maximum dimension below 1 micrometer, and more preferably from about 1 nm to about 100 nm.

In addition to the tremendous advantages relating to improved effectiveness and reduced cell damage associated with this invention, the particles of this invention have been found to provide better protection of the genetic material against nuclease degradation, and can therefore extend the period of therapeutic effectiveness.

The method of this invention involves accelerating any of the gene transfection particles disclosed herein toward a plant or animal cell with sufficient force to cause the gene transfection particle to penetrate and enter the cell. The method can be performed in vivo on cells which are normally exposed, such as epidermal cells, in vivo on cells which are exposed by surgical methods, such as tissue or cells of various internal organs, ex vivo on tissue or cell explants which are transplanted into a host plant or animal after particle bombardment, or in vitro, such as in gene amplification techniques or in the mass production of certain gene products. Particle bombardment using the gene transfection particles of this invention can be achieved using any of various gene guns which are now well known in the art and the literature, including high-voltage electric discharge apparatus, pressure discharge apparatus, and other suitable means which have or will be developed. The gas used in the pressure discharge apparatus should be essentially inert to the support, genetic material and polymer. Suitable inert gases include, for example, helium and argon.

Further understanding will be facilitated by reference to the following, non-limiting, illustrative examples.

EXAMPLE 1

A dendrimer-gold conjugate was prepared by mixing 500 μl of a 1.0 mM solution of a G4.T PAMAM dendrimer with 500 μl of a 10.15 mM solution of $HAuCl_4$, 10 μl of a solution of 35% hydrazine in water, and 2 ml (2000 μl) of water, at room temperature. ("G4.T" denotes a fourth generation PAMAM dendrimer in which the amine terminals are modified by reaction with tris-hydroxy methyl aliphatic surface groups.) Formation of the dendrimer-gold conjugates was confirmed by ultraviolet spectroscopy.

EXAMPLE 2

The dendrimer-gold conjugate of Example 1 can be contacted with any of various genetic materials to form a highly efficient gene transfection particle.

It will be apparent to those skilled in the art that various modifications to the preferred embodiment of the invention as described herein can be made without departing from the spirit or scope of the invention as defined by the appended claims.

What is claimed is:

1. A gene transfection particle comprising a composite material including: a dendritic polymer; and a metal selected from the group consisting of one or more gold, silver, copper, magnesium, or calcium particles, gold sols, gold atoms, gold ions, gold containing complexes or molecules, and clusters or a mixture thereof conjugated with the dendritic polymer, wherein the maximum dimension of the conjugate is from about 1 nm to about 1000 nm; and the conjugate further conjugated to genetic material.

2. The particle of claim 1, wherein the dendritic polymer comprises amine functional groups.

3. The particle of claim 2, wherein the dendritic polymer is a PAMAM, POPAM or PEI.

4. The particle of claim 2, wherein the dendritic polymer is a PAMAM.

5. The particle of claim 1, wherein the genetic material is DNA, a DNA fragment, or an oligonucleotide.

6. The particle of claim 5, wherein the dendritic polymer comprises amine functional groups.

7. The particle of claim 6, wherein the dendritic polymer is a PAMAM.

8. The particle of claim 1, wherein the metal is in the form of a single metal atom or atoms or ions, or compounds containing a single metal atom.

9. The particle of claim 8, wherein the dendritic polymer is a polyamine.

10. The particle of claim 8, wherein the dendritic polymer is a PAMAM, POPAM or PEI.

11. The particle of claim 8, wherein the dendritic polymer is a PAMAM.

12. A gene transfection particle comprising:

a metal selected from the group consisting of one or more gold, silver, copper, magnesium, or calcium particles, gold sols, gold atoms, gold ions, gold containing complexes or molecules, and clusters or a mixture thereof; and a dendritic polymer attached to the surface of the metal, wherein the maximum dimension of the metal and dendritic polymer conjugate is from about 1 nm to about 1000 nm; and genetic material conjugated to the metal and dendritic polymer conjugate.

13. The gene transfection particle of claim 12, wherein the maximum dimension of the gene transfection particle is from about 1 nm to about 1000 nm.

14. The gene transfection particle of claim 12, wherein the maximum dimension of the gene transfection particle is from about 1 nm to about 100 nm.

15. A method for delivering genetic material to plant or animal cells comprising:

conjugating a dendritic polymer to a metal selected from the group consisting of one or more gold, silver, copper, magnesium, or calcium particles, gold sols, gold atoms, gold ions, gold containing complexes or molecules, and clusters or a mixture thereof to form a polymer-metal conjugate, wherein the maximum dimension of the conjugate is from about 1 nm to about 1000 nm;

conjugating genetic material to the polymer-metal conjugate to form a gene transfection particle; and accelerating the gene transfection particle toward a plant or animal cell with sufficient motive force to cause the gene transfection particle to penetrate and enter the cell.

16. The method of claim 15, wherein the gene transfection particle is accelerated with a high-voltage electric discharge.

17. The method of claim 15, wherein the gene transfection particle is accelerated with pressure discharge.

18. The method of claim 15, wherein the gene transfection particle is accelerated into a cell in vivo.

* * * * *